United States Patent [19]

Weaver

[11] Patent Number: 5,549,707
[45] Date of Patent: Aug. 27, 1996

[54] FLUID COLLECTION APPARATUS

[75] Inventor: Richard A. Weaver, Linden, Mich.

[73] Assignee: Contour Fabricators, Inc., Grand Blanc, Mich.

[21] Appl. No.: 183,184

[22] Filed: Jan. 18, 1994

[51] Int. Cl.⁶ .................................................. A61M 1/00
[52] U.S. Cl. ........................ 604/317; 604/318; 604/356; 220/501; 220/4.16
[58] Field of Search ........................ 5/617; 604/317–319, 604/322, 326, 356, 357; 588/258, 255, 900; 4/450, 456, 565.1, 564.1, 566.1; 220/4.12, 4.16, 501, 666

[56] References Cited

U.S. PATENT DOCUMENTS

| | | | |
|---|---|---|---|
| 3,926,233 | 12/1975 | Brendling | 604/350 X |
| 4,445,884 | 5/1984 | Kurtz et al. | 604/317 |
| 5,092,858 | 3/1992 | Benson et al. | 604/319 |
| 5,107,857 | 4/1992 | Linnemann et al. | 128/845 |
| 5,176,667 | 5/1993 | DeBring | 604/356 |

FOREIGN PATENT DOCUMENTS

| | | | |
|---|---|---|---|
| 0127474 | 12/1984 | European Pat. Off. | |
| 333075 | 9/1989 | European Pat. Off. | 220/666 |
| 2606805 | 9/1977 | Germany | 220/501 |
| 1349517 | 4/1974 | United Kingdom | |
| 1528611 | 10/1978 | United Kingdom | |
| 93017930 | 9/1993 | WIPO | 220/4.16 |

Primary Examiner—David H. Willse
Assistant Examiner—Mark O. Polutta
Attorney, Agent, or Firm—Learman & McCulloch

[57] ABSTRACT

Fluid collection apparatus comprises a body formed of flexible material defining a chamber divided by partitions into a plurality of compartments. One of the compartments is connected by an inlet to a source of fluid which, when admitted to such compartment, enables the body to erect from a collapsed condition to an erected condition. As fluid rises in the compartment to which it is admitted, it reaches the level of openings which permit fluid to flow from the inlet compartment into adjacent compartments, and thereby erect the entire body.

22 Claims, 2 Drawing Sheets

FLUID COLLECTION APPARATUS

This invention relates to fluid collection apparatus and more particularly to apparatus especially for use in collecting and stiffening spent fluids resulting from the performance of surgical, urological, and other procedures that result in abnormal drainage of body fluids.

BACKGROUND OF THE INVENTION

A number of surgical, urological, embalming, and other procedures result in the creation and drainage of body fluids or fluids used to flush body areas. Surgeons, dentists, veterinarians, and morticians, among others, perform procedures which necessitate the provision of apparatus for collecting spent fluids. Heretofore, the collection apparatus has consisted primarily of open containers into which the fluids are discharged. Such collection apparatus, however, has a number of undesirable characteristics such as instability, difficulty in handling, and effective storage until such time as the collected fluids can be disposed of.

Another difficulty with known collection apparatus is that the technician responsible for ensuring that the fluids are collected often is hampered by the position occupied by the collection apparatus at the time the collection operation is performed.

Apparatus constructed in accordance with the invention overcomes the disadvantages of the known collection apparatus.

SUMMARY OF THE INVENTION

Fluid collection apparatus constructed in accordance with the invention comprises a body having top, bottom, side, and end walls forming a chamber within which is a plurality of partitions which divide the chamber into a plurality of compartments. The walls and partitions are formed of flexible material which enables the body to occupy a collapsed condition prior to use.

A fluid receiver is located in a position to receive spent fluids from the surgical or other procedure and has an outlet coupled by a flexible tube to an inlet formed in the top wall of the body and in communication with one of the compartments. As fluid drains from the receiver into the compartment via the inlet the collapsed body is erected. When the fluid that is introduced to the one compartment reaches a predetermined level additional fluid may pass from such compartment into other compartments via openings formed in the partitions. The flow of fluid into the other compartments will result in further erection of the body, thereby providing considerable stability against inadvertent tipping of the body. However, tipping of the body will not result in spillage of the contents since the body is closed.

The inlet to the interior of the body preferably comprises an elongate, flexible hose having its lower end in sealed communication with an opening formed in the top wall of the body. The opposite end of the hose is secured to the bottom of a receiver into which the fluids are directed by the operator for discharge through the hose into the collection chamber.

Preferably, the side and end walls of the body are provided with extensions that form a pouch above the level of the body's top wall and of such size as to accommodate the inlet hose and the receiver. The pouch is provided with closure means operable selectively to open and close the pouch.

Flaps are provided on two opposite sides of the body to form carrying handles for facilitating carrying the body when it is full of fluid.

THE DRAWINGS

The presently preferred form of fluid collection apparatus is illustrated in the accompanying drawings, wherein.

THE PREFERRED EMBODIMENT

Figure 1:
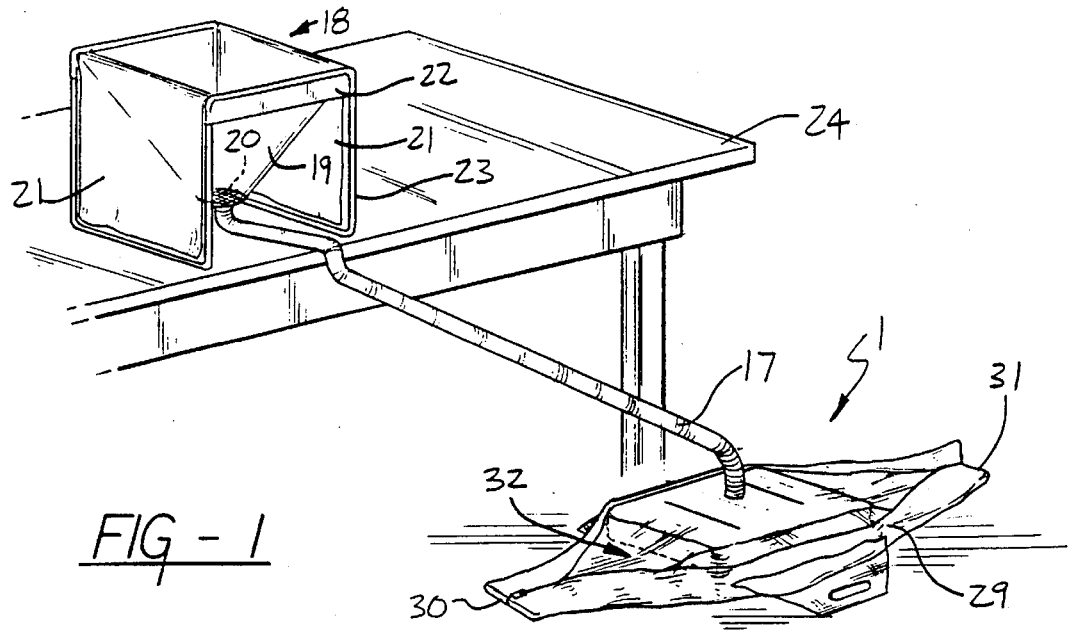
FIG. 1 is a fragmentary, isometric view of the apparatus at the beginning of a filling operation.
Figure 2:
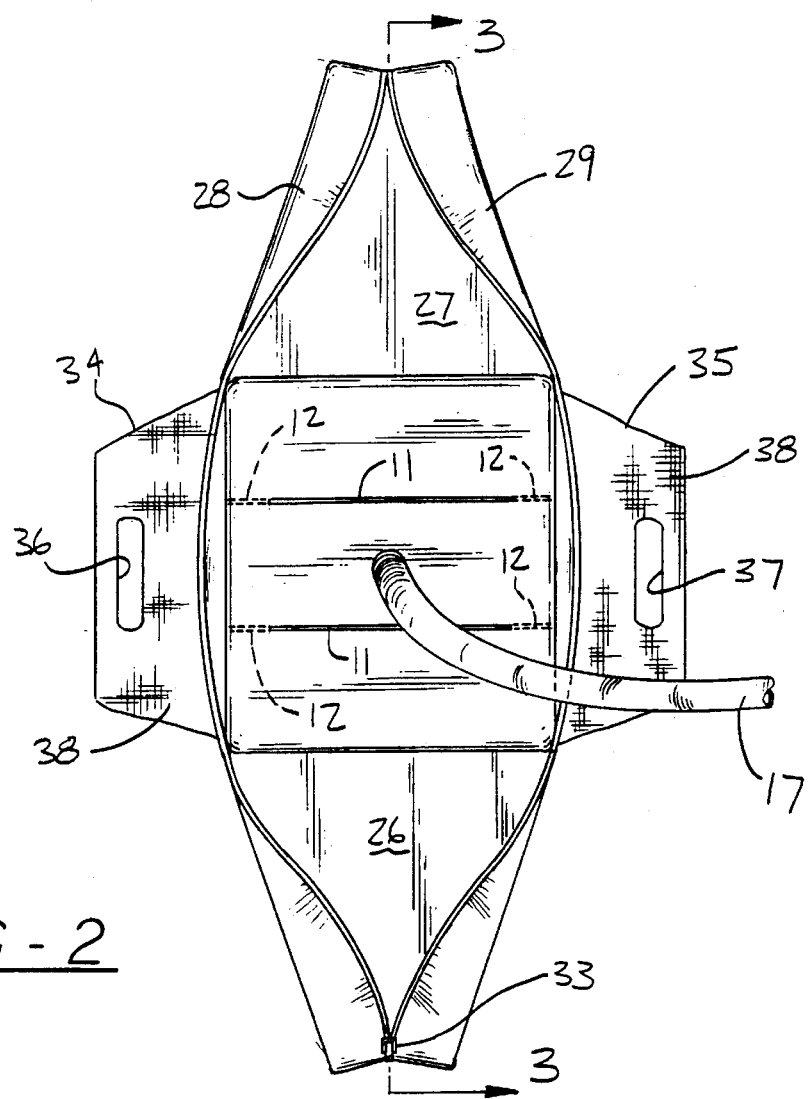
FIG. 2 is an enlarged, fragmentary, top plan view of the collector.

Collection apparatus constructed in accordance with the presently preferred embodiment of the invention is designated generally by the reference character 1 and comprises a body 2 having a top wall 3, a bottom wall 4, opposite side walls 5 and 6, and opposite end walls 7 and 8. All of the walls are joined and sealed to one another to form a closed chamber 9 within the body.

At spaced intervals within the compartment 9 is a plurality of partitions 10 which are sealed at their respective lower and opposite ends to the bottom wall 4 and the side walls 5 and 6 of the body. Each partition also is sealed by means of a seam 11 to the top wall 3 of the body, but each seam terminates short of the side walls 5 and 6 so as to provide openings 12 at opposite ends of each partition 10 and at the level of the inner surface of the top wall 3.

The partitions 10 divide the chamber 9 into a plurality of compartments 13, 14, and 15. In the disclosed embodiment the compartment 14 is located between the compartments 13 and 15 and is in communication with each of the adjacent compartments via the openings 12.

Figure 3:
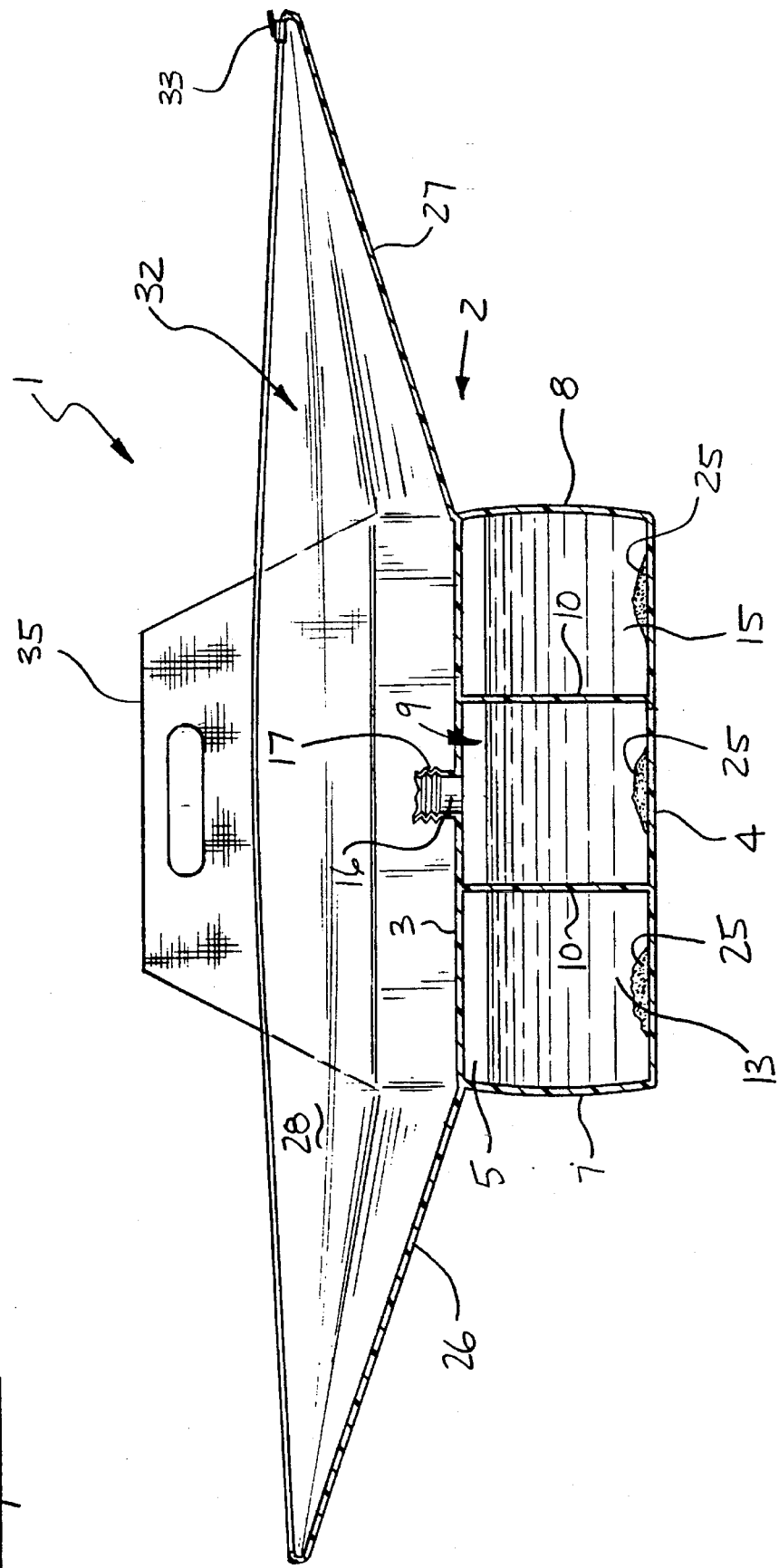
FIG. 3 is a sectional view taken on the line 3—3 of FIG. 2 and showing the collector in an erected, substantially filled condition.

The material from which the walls and partitions of the body 2 is formed is waterproof and sufficiently flexible to enable the body to assume a collapsed condition, as shown in FIG. 1, or an erected condition as shown in FIG. 3. A suitable material from which the body may be formed is 8 mil polyvinylchloride film.

The top wall 3 of the compartment 14 has an opening in which a rigid nipple 16 is cemented. Cemented or otherwise sealingly fixed to the nipple is one end of a flexible hose 17, the opposite end of which extends toward a receiver 18. The hose is of such length as to enable the collector body 2 to be located in a position well clear of the operator's feet.

The receiver comprises an inverted pyramidal or conical receptacle 19 having at its bottom a nipple like the nipple 16 to which the hose 17 is cemented. At the bottom of the receptacle 19 and at a level above that of the connection of the hose 17 to the nipple is a filter or screen 20. The receiver 18 has side flaps 21 and end skirts 22 which may be used to support the receptacle 18 in an upright condition on a suitable wire or other frame 23 and in such position as to enable the receptacle 19 to receive fluids from whatever procedure is being performed by the physician or technician.

In the operation of the apparatus thus far described, the receiver 18 is fitted to the frame 23 which may be placed upon a support 24 such as a table or the like. The hose 17 is of such length as to enable the collection apparatus 1 to be placed on the floor at a level below that of the receiver 18 and enable fluids from the container 18 to flow by gravity through the hose 17 into the chamber 9 of the body 2.

At the commencement of operations, the body 2 will be in a collapsed condition as is shown in FIG. 1.

The difference in the levels of the receiver 18 and the body 2 is such that fluid in the receiver provides a head sufficient to cause fluid entering the compartment 14 to erect the walls and partitions forming the compartment 14. As the walls of the compartment 14 erect, those parts of the body on opposite sides of the partition provide sufficient stability to minimize the risk of tipping of the body 2. Even if the body should tip, however, the compartment 9 is completely sealed except for the inlet opening at its upper end, and such inlet also is sealed via the sealing connection of the hose 17 to the nipple 16.

As fluid rises in the compartment 14 it eventually will reach the level of the openings 12 whereupon fluid will pass into the compartments 13 and 15, erecting the walls defining such compartments. When all the compartments are full, or nearly so, the body comprises an extremely stable container for the fluid accommodated therein.

Preferably, each compartment 13–15 contains a small quantity of a gelling agent that is operable to gel or stiffen the fluid within the chamber 9. There are many suitable gelling agents, one of which is a cross-linked polyacrylamide sold under the trademark HYDROSOURCE. The gelling agent initially is in powdered form and is indicated in FIG. 3 by the reference character 25.

Secured to the opposite side and end walls of the body 2, and at the level of the top wall 3, are extensions of the same material from which the body is formed. There are two end extensions 26 and 27 and two side extensions 28 and 29. The extensions are sealed to one another at their opposite ends, as indicated at 30 and 31, thereby forming a pouch 32 of such size as to accommodate the receiver 18 and the hose 17. To place the receiver 18 in the pouch 32, the receiver is removed from its supporting frame 23 and folded, together with the hose 17, into a bundle which may be accommodated in the pouch 32.

Preferably, the confronting edges of the extensions 28 and 29 are shaped to cooperate with a slide fastener 33 constituting a closure which is operable selectively to open and close the pouch 32. Following the placing of the folded receptacle and hose in the pouch 32 and closing of the latter by the closure 33, the opposite ends of the pouch-forming extensions then may be folded over one another to form a compact unit.

The side extensions 28 and 29 preferably are provided with flaps 34 and 35 having openings 36 and 37 therein for the accommodation of a person's fingers. The flaps may be raised to a position confronting one another so as to provide a convenient carrying support for the container 1 and its contents. If desired, one or both sides of each of the flaps 35 may include reinforcing material 38, such as a reinforced vinyl laminate sold by Herculite Products, Inc. of New York, N.Y., under the trademark STAPHCHEK.

The entire container 1, and its contents, may be delivered to an incinerator for disposal.

The disclosed embodiment is representative of the presently preferred form of the invention, but is intended to be illustrative rather than definitive thereof. The invention is defined in the claims.

I claim:

1. Fluid collection apparatus comprising a body having top, bottom, side, and end walls forming a chamber; partition means within said chamber sealed to said top, bottom, and side walls and forming in said chamber a plurality of compartments; and inlet means in communication with one of said compartments from outside said chamber for admitting a fluid to said one of said compartments, said walls and said partition means being formed of material sufficiently flexible to enable said body to erect from a collapsed condition in response to the flow of fluid into said one of said compartments via said inlet means, the partition means between said one of said compartments and each adjacent compartment having an opening therein at a level above that of said bottom wall for enabling fluid to flow from one of said compartments into each adjacent compartment only in response to the level of fluid in said one of said compartments rising above said bottom wall to the level of said opening, said side and end walls having extensions which provide a pouch above the level of said top wall.

2. Apparatus according to claim 1 wherein said inlet means is in said top wall.

3. Apparatus according to claim 2 wherein said opening is adjacent the level of said top wall.

4. Apparatus according to claim 1 including a gelling agent in at least said one of said compartments for gelling fluid in said one of said compartments.

5. Apparatus according to claim 1 including a gelling agent in each of said compartments for gelling fluid therein.

6. Apparatus according to claim 1 including closure means for selectively opening and closing said pouch.

7. Apparatus according to claim 1 wherein said inlet means comprises a hose having one of its ends secured to said top wall and its other end secured to and extending downwardly from a receiver.

8. Apparatus according to claim 7 wherein said receiver comprises a receptacle having downwardly converging side walls and a screen in said receptacle at its lower end.

9. Apparatus according to claim 8 wherein said pouch is of such size as to accommodate said receptacle.

10. Apparatus according to claim 9 wherein two of said extensions have flaps providing supports to facilitate carrying said body.

11. Apparatus according to claim 10 wherein each of said flaps includes reinforcing means.

12. Fluid collection apparatus comprising a body having top, bottom, side, and end walls forming a closed chamber; at least one partition in said chamber sealed to said top, bottom, and side walls and dividing said chamber into at least two compartments; and inlet means in sealed communication with one of said compartments for admitting a fluid thereto, at least said side and end walls and said partition being formed of material sufficiently flexible to enable said body to erect vertically from a collapsed condition in response to the flow of fluid into said one of said compartments via said inlet means, said partition having an opening therein in communication with both of said compartments at a level above the bottom wall and adjacent said top wall to enable fluid to flow from said one of said compartments into the other only in response to the erection of said one of said compartments and the rising the level of fluid in said one of said compartments above the bottom wall to the level of said opening.

13. Apparatus according to claim 12 wherein said inlet means is in communication with said one of said compartments via said top wall.

14. Apparatus according to claim 12 including extensions of said side and end walls which provide a pouch above the level of said top wall.

15. Apparatus according to claim 14 wherein said pouch is of such size as to accommodate said inlet means.

16. Apparatus according to claim 14 including closure means for selectively opening and closing said pouch.

17. Apparatus according to claim 12 wherein two of said extensions have flaps providing handles to facilitate carrying said body.

18. Apparatus according to claim 17 wherein each of said flaps includes reinforcing means.

19. Liquid collection apparatus comprising a body having top, bottom, side, and end walls forming a chamber; two partitions within said chamber sealed to said top, bottom, and side walls and forming in said chamber three compartments one of which occupies a position between the other two; and inlet means in communication with said one of said compartments via its top wall for admitting liquid from outside said chamber to said one of said compartments, said walls and said partitions being formed of material sufficiently flexible to enable said body to erect vertically from a flattened, collapsed condition solely in response to the flow of liquid into said one of said compartments via said inlet means, the partition between said one of said compartments and each adjacent compartment having an opening therein at a level adjacent said top wall and through which liquid may flow from said one compartment into each of the adjacent compartments only in response to the erection of said one of said compartments and after the level of liquid in said one compartment rises to the level of the opening in the associated partition.

20. Apparatus according to claim 19 wherein the opening in each of said partitions is adjacent one of said side walls.

21. Apparatus according to claim 19 wherein each of said partitions has a pair of spaced apart openings therein, one of said openings being adjacent one of said side walls and the other of said openings being adjacent the opposite side wall.

22. Apparatus according to claim 19 wherein said inlet means includes a liquid delivery tube in sealed communication with said one compartment.

* * * * *